US009575053B2

(12) United States Patent
Nakayama et al.

(10) Patent No.: US 9,575,053 B2
(45) Date of Patent: Feb. 21, 2017

(54) URINARY BIOMARKER FOR USE IN TEST FOR PROSTATE CANCER

(71) Applicant: KYOTO UNIVERSITY, Kyoto-shi, Kyoto (JP)

(72) Inventors: Kenji Nakayama, Kyoto (JP); Kazuharu Shimizu, Kyoto (JP); Jun Utsumi, Kyoto (JP); Takahiro Inoue, Kyoto (JP); Osamu Ogawa, Kyoto (JP)

(73) Assignee: KYOTO UNIVERSITY, Kyoto-Shi (JP)

( * ) Notice: Subject to any disclaimer, the term of this patent is extended or adjusted under 35 U.S.C. 154(b) by 25 days.

(21) Appl. No.: 14/389,320

(22) PCT Filed: Mar. 28, 2013

(86) PCT No.: PCT/JP2013/059208
§ 371 (c)(1),
(2) Date: Sep. 29, 2014

(87) PCT Pub. No.: WO2013/146997
PCT Pub. Date: Oct. 3, 2013

(65) Prior Publication Data
US 2015/0065373 A1 Mar. 5, 2015

(30) Foreign Application Priority Data

Mar. 30, 2012 (JP) .................................. 2012-078963

(51) Int. Cl.
| | |
|---|---|
| *G01N 33/53* | (2006.01) |
| *G01N 33/493* | (2006.01) |
| *G01N 33/574* | (2006.01) |
| *G01N 33/68* | (2006.01) |
| *C12N 9/64* | (2006.01) |

(52) U.S. Cl.
CPC ........... *G01N 33/493* (2013.01); *C12N 9/6424* (2013.01); *G01N 33/57434* (2013.01); *G01N 33/6851* (2013.01); *C12Y 304/21077* (2013.01)

(58) Field of Classification Search
None
See application file for complete search history.

(56) References Cited

U.S. PATENT DOCUMENTS

| | | |
|---|---|---|
| 5,807,978 A | 9/1998 | Kokolus et al. |
| 6,326,471 B1 | 12/2001 | Kokolus et al. |
| 6,929,918 B1* | 8/2005 | Charrier ............ G01N 33/57434 424/184.1 |
| 6,946,133 B1 | 9/2005 | Schlom et al. |
| 7,872,104 B2 | 1/2011 | Pettersson et al. |
| 2005/0130899 A1 | 6/2005 | Itoh |
| 2012/0252040 A1 | 10/2012 | Yoon et al. |

FOREIGN PATENT DOCUMENTS

| | | | |
|---|---|---|---|
| JP | 11-178580 | A | 7/1999 |
| JP | 2000-506520 | A | 5/2000 |
| JP | 2005-511037 | A | 4/2005 |
| JP | 3782100 | B2 | 6/2006 |
| JP | 4035845 | B2 | 1/2008 |
| JP | 2008-202978 | A | 9/2008 |
| JP | 2011-500718 | A | 1/2011 |
| WO | WO 94/03205 | A1 | 2/1994 |
| WO | WO 97/29199 | A2 | 8/1997 |
| WO | WO 03/047506 | A2 | 6/2003 |
| WO | WO 2009/052328 | A1 | 4/2009 |

OTHER PUBLICATIONS

Watt et al (PNAS, 1986, 83: 3166-3170).*
Bolduc et al (Can Urol Assoc, 2007, 1(4): 377-381).*
Stovsky et al (Urology, 2011, 78(3): 601-605).*
Bolduc et al (Can Urol Assoc, 2009, 3(3): 213-217).*
Shibata et al (Biochimica et Biophysica Acta, 1997, 425-433).*
M'Koma et al (Biochem Biophys Res Commun, 2007, 353(3): 829-834).*
Adachi et al., "The human urinary proteome contains more than 1500 proteins, including a large proportion of membrane proteins", Genome Biol., vol. 7, No. 9, 2006, 1 page, only abstract provided.
Afkarian et al., "Optimizing a proteomics platform for urine biomaker discovery", Mol. Cell. Proteomics., vol. 9, No. 10, Oct. 2010 (Published online May 28, 2010), 1 page, only abstract provided.
American Cancer Society, "Cancer Facts & Figures 2010", Atlanta: American Cancer Society, 2010, 68 pages.
Cancer Information Service, Center for Cancer Control and Information Services, National Cancer Center, Japan, 2015, 2 pages, url: http://ganjoho.jp/professional.index.html.
Chou et al., "Prostate Cancer Screening—The Evidence, the Recomendations, and the Clincal Implications", JAMA, vol. 306, No. 24, 2011, 1 page, pp. 2721-2722, only abstract provided.
De Bock et al., "Challenges for biomaker discovery in body fluids using SELDI-TOF-MS.", J. Biomed Biotechnol., 2010 (Published online Dec. 6, 2009), 1 page, only abstract provided.
Gandini et al., "Correspondence re: J.B. de Kok et al., DD3 A very Sensitive and Specific Marker to Detect Prostate Tumors", Cancer Research, vol. 63, Aug. 1, 2003, p. 4747.
Lee et al., "Prostate cancer: Diagnostic performance of the PCA3 urine test", Nature Reviews Urology, vol. 8, Mar. 2011, pp. 123-124, only abstract provided.

(Continued)

*Primary Examiner* — Sean Aeder
(74) *Attorney, Agent, or Firm* — Birch, Stewart, Kolasch & Birch, LLP (57) ABSTRACT

A novel method that enables prostate cancer testing that is noninvasive and more accurate than conventional methods is disclosed. The present inventors intensively analyzed urine samples from prostate cancer patients, and non-cancer subjects, who are free of prostate cancer, and, as a result, newly discovered urinary peptides that can be used as indicators in prostate cancer testing. Use of these urinary peptides as indicators enables various prostate cancer-related tests including detection of prostate cancer, discrimination between prostate cancer and benign prostatic hyperplasia, monitoring of a therapeutic effect of prostate cancer therapy and monitoring of postoperative recurrence.

9 Claims, 4 Drawing Sheets

(56) References Cited

OTHER PUBLICATIONS

Michel et al., "Involement of the C-terminal end of the prostate-specific antigen in a conformational epitote: characterization by proteolytic degradation of monoclonal antibody-bound antigen and mass spectrometry", Journal of Molecular Recognition, vol. 14, 2001, pp. 406-413.

Norden et al., "Quantitative amino acid and proteomic analysis: very low excretion of polypeptides>750 Da in normal urine", Kidney Int., vol. 66, No. 5, Nov. 2004, 1 page, pp. 1994-2003, only abstract provided.

Okamoto et al., "Protein profiling of post-prostatic massage urine specimens by surface-enhanced laser desorption/ionization time-of-flight mass spectrometry to discriminate between prostate cancer and benign lesions", Oncol Rep., vol. 21, No. 1, Jan. 2009, 1 page, pp. 73-79, only abstract provided Theodorescu et al., "Discovery and validation of urinary biomarkers for prostate cancer", Proteomics Clin Appl., vol. 2, No. 4, Mar. 7, 2008, 1 page, pp. 556-570, only abstract provided.

Wang et al., "Purification of a human prostate specific antigen", Invest Urol., vol. 17, No. 2, Sep. 1979, 1 page, pp. 159-163, only abstract provided.

Adachi et al., "The human urinary proteome contains more than 1500 proteins, including a large proportion of membrane proteins", Genome Biol., vol. 7, No. 9, (2006) pp. R.90.1-R.90.16.

Afkarian et al., "Optimizing a proteomics platform for urine biomarker discovery", Mol. Cell. Proteomics., vol. 9, No. 10, (May 2010) pp. 2195-2204.

Chou et al., "Prostate Cancer Screening—The Evidence, the Recommendations, and the Clinical Implications", JAMA, vol. 306, No. 24 (2011) pp. 2721-2722.

De Bock et al., "Challenges for biomarker discovery in body fluids using SELDI-TOF-MS.", J. Biomed Biotechnol., (2010) pp. 1-15.

Norden et al., "Quantitative amino acid and proteomic analysis: very low excretion of polypeptides>750 Da in normal urine", Kidney Int., vol. 66, No. 5 (Nov. 2004) pp. 1994-2003.

Theodorescu et al., "Discovery and validation of urinary biomarkers for prostate cancer", Proteomics Clin Appl., vol. 2, No. 4, (2008) pp. 556-570.

Wang et al., "Purification of a human prostate specific antigen", Invest Urol., vol. 17, No. 2 (1979) pp. 159-163.

de Kok et al., "DD3PCA3, a Very Sensitive and Specific Marker to Detect Prostate Tumors", Cancer Research, vol. 62, (2002) pp. 2695-2698.

Lee et al., "Diagnostic Performance of the PCA3 Urine Test", Nat. Rev. Urol., vol. 8 (2011) pp. 123-124.

Extended European Search Report dated Feb. 23, 2016, for European Application No. 13770375.7.

Nakayama et al., "The C-Terminal Fragment of Prostate-Specific Antigen, a 2331 Da Peptide, as a New Urinary Pathognomonic Biomarker Candidate for Diagnosing Prostate Cancer," PLOS ONE, vol. 9. Issue 9, e107234, Sep. 2014, pp. 1-13.

Okamoto et al., "Protein profiling of post-prostatic massage urine specimens by surface-enhanced laser desorption/ionization time-of-flight mass spectrometry to discriminate between prostate cancer and benign lesions", Oncology Reports, vol. 21, 2009, pp. 73-79.

\* cited by examiner

(A)
Mass Profile of Urinary Peptides/Protein Fragments Obtained Using MALDI-TOF/MS$^n$

Analysis Using MALDI-TOF/MS²
(MS² Spectrum of m/z 2332)

Fig.2

Analysis Using MALDI-TOF/MS²
(MS² Spectrum of m/z 1243)

LRLSEPAELTD

SEQUENCE LISTING

<160> NUMBER OF SEQ ID NOS: 6

<210> SEQ ID NO 1
<211> LENGTH: 19
<212> TYPE: PRT
<213> ORGANISM: Homo sapiens

<400> SEQUENCE: 1

Tyr Thr Lys Val Val His Tyr Arg Lys Trp Ile Lys Asp Thr Ile Val
1               5                   10                  15

Ala Asn Pro

<210> SEQ ID NO 2
<211> LENGTH: 11
<212> TYPE: PRT
<213> ORGANISM: Homo sapiens

<400> SEQUENCE: 2

Leu Arg Leu Ser Glu Pro Ala Glu Leu Thr Asp
1               5                   10

<210> SEQ ID NO 3
<211> LENGTH: 12
<212> TYPE: PRT
<213> ORGANISM: Homo sapiens

<400> SEQUENCE: 3

Leu Arg Leu Ser Glu Pro Ala Glu Leu Thr Asp Ala
1               5                   10

<210> SEQ ID NO 4
<211> LENGTH: 21
<212> TYPE: PRT
<213> ORGANISM: Homo sapiens

<400> SEQUENCE: 4

Leu Leu Lys Asn Gly Glu Arg Ile Glu Lys Val Glu His Ser Asp Leu
1               5                   10                  15

Ser Phe Ser Lys Asp
                20

<210> SEQ ID NO 5
<211> LENGTH: 261
<212> TYPE: PRT
<213> ORGANISM: Homo sapiens

<400> SEQUENCE: 5

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
                20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
        50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
                100                 105                 110

```
Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
        130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
        210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
                260

<210> SEQ ID NO 6
<211> LENGTH: 119
<212> TYPE: PRT
<213> ORGANISM: Homo sapiens

<400> SEQUENCE: 6

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

URINARY BIOMARKER FOR USE IN TEST FOR PROSTATE CANCER

TECHNICAL FIELD

The present invention relates to a novel urinary biomarker for prostate cancer testing.

BACKGROUND ART

Prostate cancer is a malignant disease that is prevalent in Western countries, and it is also becoming remarkably prevalent in Japan (Non-patent Document 1). The number of deaths from prostate cancer in Japan in 2009 exceeded 10,000 to reach 10,036, and is still increasing (Non-patent Document 2). Therefore, there is also a social demand for improvement of the diagnostic technique and development of a new therapeutic method for prostate cancer.

The prostate-specific antigen (PSA), which was separated from seminal plasma in 1979 by Wang et al., is a glycoprotein having a molecular weight of 34 kDa composed of 237 amino acids, and is a substance identical to human kallikrein 3 (Non-patent Document 3). Measurement of serum PSA is currently widely used not only for diagnosis and judgment of recurrence of prostate cancer, but also for prognostication, and judgment of therapeutic effects. Although serum PSA has good detection sensitivity for prostate cancer, its specificity for detection of cancer is low, since it is a prostate-specific antigen rather than a prostate cancer-specific antigen and PSA may also increase in cases of a benign disease such as benign prostatic hyperplasia or prostatitis, or rectal examination or ejaculation. Therefore, in cases where the reference value 4 ng/mL is used as the serum PSA cutoff in work-up, the false-positive rate is high, and this results in unnecessary prostatic biopsy which imposes physical burden on the patient. It is actually said that, in the so-called gray zone, where the serum PSA value is 4 to 10 ng/mL, the positive rate of prostate cancer is 25 to 30%, and that unnecessary biopsy is carried out in about 70% of the cases within this range (Non-patent Document 4). Thus, a new biomarker that allows non-cancer patients to avoid unnecessary biopsy and enables more efficient detection of prostate cancer patients than serum PSA is being strongly demanded.

Improvement of the method of collection of clinical samples from patients is also demanded. Although blood is a common clinical sample, the amount of blood that can be sampled may be limited in cases where blood samples need to be frequently collected in monitoring of disease over time. Use of a clinical sample whose collection is less burdensome for patients is more preferred. Urine is excreted every day and can be noninvasively collected, and urinary markers are ideal materials for examination also from an ethical point of view. Moreover, since the duct of the prostate opens at the urethra, various substances directly secreted from the prostate can be detected by comparing spot urine with post-prostatic massage urine. Actually, known diagnostic methods using a urine sample include (1) urinary RNAs, (2) urinary DNAs, (3) urinary proteins or (4) urinary metabolites. Among these, the prostate cancer gene 3 (PCA3), which encodes a non-coding RNA, has been reported to show high expression in prostate cancer but low expression in a normal prostate (Non-patent Document 5), and some diagnostic methods for prostate cancer by detection of urinary PCA3 have been reported in recent years (Non-patent Document 6). However, at clinical sites, such methods are still inferior to examination of serum PSA, and diagnostic methods using other urinary components are still being studied. Thus, establishment of a novel method for prostate disease testing using a urinary peptide or protein fragment associated with the disease is of high clinical significance.

Urine contains various peptides and protein fragments having molecular weights of not more than 10 kDa, and the amount of these peptides and fragments excreted reaches several ten milligrams per day even in healthy individuals (Non-patent Document 7). Urine can be noninvasively sampled, has only low activity of protease, and contains substances derived from blood, kidney, bladder, ovary, prostate and the like. Therefore, multifaceted proteomics studies targeting proteins having molecular weights of not less than 10 kDa are being carried out in search of disease-associated markers (Non-patent Documents 8 and 9).

Examples of the common method for comprehensive analysis of peptides and proteins include two-dimensional electrophoresis and liquid chromatography. However, such methods are suitable for molecular fractions corresponding to molecular weights of not less than 10,000, and they are not suitable for specific detection of low-molecular-weight proteins and peptides. A protein chip technology by the combination of Surface Enhanced Laser Desorption/Ionization (SELDI) and Time-of-flight/Mass spectrometry: (TOF/MS) was developed and utilized for detection of novel tumor markers and the like (Non-patent Document 10). However, since structure determination (amino acid sequence determination) cannot be done with disease-associated marker peaks detected by SELDI-TOF/MS, the method is not suitable for confirmatory clinical tests.

In terms of prostate cancer, Theodorescu et al. performed capillary electrophoresis (CE)-TOF/MS analysis of urine samples, and 12 peptide peaks were detected and identified. These peaks were reported as candidates for prostate cancer-associated markers (Non-patent Document 11), but they have not been practically used yet. Okamoto et al. used urine voided after prostatic massage as samples to perform SELDI-TOF/MS analysis within the mass range of m/z 2,500 to 150,000 using sinapic acid as a matrix, and detected 72 peaks significantly different from the peaks observed for benign prostatic hyperplasia (Non-patent Document 12). However, since most of the detected peaks have not been identified, they have not been clinically applied.

Patent Documents 1 to 8, which aim at industrial application, disclose short PSA fragments of not more than about 20 to 30 residues. All of these are peptides each composed of a region that induces a specific biological effect such as an epitope, identified by analysis of the PSA sequence, and are not natural products but artificial products. There is no disclosed information on the fact that urine actually contains such short PSA fragments and that such fragments can be used as markers for prostate cancer testing, and none of these fragments has been practically used for clinical tests.

PRIOR ART DOCUMENTS

Patent Documents

Patent Document 1: JP 3782100 B
Patent Document 2: JP 4035845 B
Patent Document 3: JP 2011-500718 A
Patent Document 4: JP 2000-506520 A
Patent Document 5: U.S. Pat. No. 6,946,133 B Patent Document 6: U.S. Pat. No. 5,807,978 B
Patent Document 7: U.S. Pat. No. 6,326,471 B
Patent Document 8: JP 4364643 B Non-Patent Documents Non-patent Document 1: American Cancer Society. (2010) Cancer facts and Figures 2010, Atlanta: American Cancer Society.
Non-patent Document 2: Cancer Information Service, Center for Cancer Control and Information Services, URL: world wide web.ganjoho.jp/professional/index.html
Non-patent Document 3: Wang M C, et al. (1979) Purification of a human prostate specific antigen. Invest Urol. 17:159-63.
Non-patent Document 4: Chou R, et al. (2011) Prostate cancer screening—the evidence, the recommendations, and the clinical implications. JAMA. 306:2721-2722.
Non-patent Document 5: de Kok J B, et al. (2002) DD3 (PCA3), a very sensitive and specific marker to detect prostate tumors. Cancer Res. 62:2695-2698.
Non-patent Document 6: Lee G L, et al. (2011) Prostate cancer: diagnostic performance of the PCA3 urine test. Nat Rev Urol. 8:123-124.
Non-patent Document 7: Norden A G, et al. (2004) Quantitative amino acid and proteomic analysis: very low excretion of polypeptides >750 Da in normal urine. Kidney Int. 66:1994-2003.
Non-patent Document 8: Adachi J, et al. (2006) The human urinary proteome contains more than 1500 proteins, including a large proportion of membrane proteins. Genome Biol. 7:R80.
Non-patent Document 9: Afkarian M, et al. (2010) Optimizing a proteomics platform for urine biomarker discovery. Mol Cell Proteomics. 9:2195-2204.
Non-patent Document 10: De Bock M, et al. (2010) Challenges for biomarker discovery in body fluids using SELDI-TOF-MS. J Biomed Biotechnol, 2010:906082.
Non-patent Document 11: Theodorescu D, et al. (2008) Discovery and validation of urinary biomarkers for prostate cancer. Proteomics Clin Appl. 2:556-570.
Non-patent Document 12: Okamoto A, et al. (2009) Protein profiling of post-prostatic massage urine specimens by surface-enhanced laser desorption/ionization time-of-flight mass spectrometry to discriminate between prostate cancer and benign lesions. Oncol Rep. 21:73-79.

SUMMARY OF THE INVENTION

Problems to be Solved by the Invention

As described above, a biomarker that has high specificity and can simply detect prostate cancer has not yet been established, and development of a useful biomarker is an important task at clinical sites. The present invention aims to provide a novel means that enables noninvasive prostate cancer testing with more accuracy than conventional methods.

Means for Solving the Problems

The present inventors intensively studied urine samples from prostate cancer patients and non-cancer subjects who are free of prostate cancer. As a result, the present inventors succeeded in identifying peptides that were significantly elevated or decreased in prostate cancer, and discovered that, by using these urinary peptides as indicators, various prostate cancer-related tests including detection of prostate cancer, discrimination between prostate cancer and benign prostatic hyperplasia, monitoring of a therapeutic effect of prostate cancer therapy and monitoring of postoperative recurrence become possible, thereby completing the present invention.

That is, the present invention provides a urinary biomarker for prostate disease testing, the biomarker being composed of at least one peptide selected from the peptides (a) to (d) below:
  (a) peptide composed of the amino acid sequence of SEQ ID NO:1;
  (b) peptide composed of the amino acid sequence of SEQ ID NO:2;
  (c) peptide composed of the amino acid sequence of SEQ ID NO:3;
  (d) peptide composed of the amino acid sequence of SEQ ID NO:4.

The present invention also provides a urinary biomarker for prostate cancer testing, the biomarker being composed of at least one peptide selected from the peptides (a) to (d) below:
  (a) peptide composed of the amino acid sequence of SEQ ID NO:1;
  (b) peptide composed of the amino acid sequence of SEQ ID NO:2;
  (c) peptide composed of the amino acid sequence of SEQ ID NO:3;
  (d) peptide composed of the amino acid sequence of SEQ ID NO:4.

The present invention further provides a urinary biomarker for prostate disease testing, the biomarker being composed of at least one peptide selected from the peptides (1) to (4) below:
  (1) peptide whose m/z is 2332±4 in mass spectrometry;
  (2) peptide whose m/z is 1243±3 in mass spectrometry;
  (3) peptide whose m/z is 1314±3 in mass spectrometry;
  (4) peptide whose m/z is 2444±4 in mass spectrometry.

The present invention further provides a urinary biomarker for prostate cancer testing, the biomarker being composed of at least one peptide selected from the peptides (1) to (4) below:
  (1) peptide whose m/z is 2332±4 in mass spectrometry;
  (2) peptide whose m/z is 1243±3 in mass spectrometry;
  (3) peptide whose m/z is 1314±3 in mass spectrometry;
  (4) peptide whose m/z is 2444±4 in mass spectrometry.

The present invention further provides a method for prostate disease testing, the method comprising analyzing a urine sample collected from a subject; and examining the urine sample for the presence or absence and/or the amount of the urinary biomarker according to the present invention described above. The present invention further provides a method for prostate cancer testing, the method comprising analyzing a urine sample collected from a subject; and examining the urine sample for the presence or absence and/or the amount of the urinary biomarker according to the present invention described above. The present invention further provides at least one peptide selected from the peptides (a) to (d) described above, for use as a urinary biomarker in prostate disease testing. The present invention further provides at least one peptide selected from the peptides (a) to (d) described above, for use as a urinary biomarker in prostate cancer testing. The present invention further provides at least one peptide selected from the peptides (1) to (4) described above, for use as a urinary biomarker in prostate disease testing. The present invention further provides at least one peptide selected from the peptides (1) to (4) described above, for use as a urinary biomarker in prostate cancer testing.

Effect of the Invention

The present invention newly provided urinary peptide markers that can be used in prostate cancer testing in various situations. Urine can be noninvasively collected, and urine markers are ideal markers from both ethical and practical viewpoints. In contrast to conventional PSA tests, in which discrimination of prostate cancer from benign prostatic hyperplasia is difficult, the present invention enables discrimination of prostate cancer from benign prostatic hyperplasia, and has better accuracy as a test method.

MODE FOR CARRYING OUT THE INVENTION

"Non-prostate cancer patients" in the present invention means patients who are not suffering from prostate cancer, and includes both healthy individuals and benign prostatic hyperplasia patients. "Non-benign prostatic hyperplasia patients" means individuals who are not suffering from benign prostatic hyperplasia, and includes both healthy individuals and prostate cancer patients. "Healthy individuals" means individuals with neither prostate cancer nor benign prostatic hyperplasia. In males, the prostate may enlarge with aging, but its treatment is unnecessary even in cases where the patient has a symptom such as bradyuria or pollakiuria as long as the patient does not feel inconvenience in daily life. It is very important to discriminate cancer, which is a severe and fatal disease, from non-fatal, non-cancer conditions.

The urinary peptides which the present inventors newly found as biomarkers available for prostate cancer testing are the peptides shown in Table 1 below.

TABLE 1

| | Peak | Peptide sequence | Origin | SEQ ID NO: |
|---|---|---|---|---|
| (1) | (a) m/z 2332 ± 4 | YTKVVHYRKWI KDTIVANP | PSA fragment 1 (aa243-261) | 1 |
| (2) | (b) m/z 1243 ± 3 | LRLSEPAELTD | PSA fragment 2 (aa124-134) | 2 |
| (3) | (c) m/z 1314 ± 3 | LRLSEPAELTD A | PSA fragment 3 (aa124-135) | 3 |
| (4) | (d) m/z 2444 ± 4 | LLKNGERIEKV EHSDLSFSKD | β2 microglobulin fragment 1 (aa59-79) | 4 |

The region of each peptide is indicated using the following full-length amino acid sequence as a standard:
human PSA NP_001639.1 (SEQ ID NO: 5)
human β2 microglobulin NP004039.1 (SEQ ID NO: 6).

The peptides (1) to (4) (the PSA fragments 1 to 3, and the (β2microglobulin fragment 1) are detected at high levels in urine of prostate cancer patients. The "high level" herein means that the level is higher than the average of the levels detected by analysis of the urinary peptide levels in a population of known non-prostate cancer patients (either a population of healthy individuals, or a population of healthy individuals+benign prostatic hyperplasia patients), and may be a value which is not less than twice as high as the above-mentioned average, although the value is not limited thereto. In healthy individuals and benign prostatic hyperplasia patients, the peptides (1) to (4) are not detected or at low levels. In cases where these peptides (1) to (4) are detected at high levels in a urinary sample derived from a subject, it can be judged that the subject is highly likely to be suffering from prostate cancer. The peptides (1) to (4) can be said to be prostate cancer markers (prostate cancer-specific urinary biomarkers). In the prior art, no reports are found on the use of the peptides (1) to (4) as markers for prostate disease testing using urine as a sample.

In Table 1, as a urinary biomarker(s) for prostate cancer testing, the peptides (1) to (4) are preferred; the peptides (1) to (3) (PSA fragments) are more preferred; and the peptide (1) is especially preferred. These peptides can be preferably used as prostate cancer-specific markers. In a conventional PSA test, discrimination between prostate cancer and benign prostatic hyperplasia is difficult, and a high level is found also in cases of benign prostatic hyperplasia. In contrast, by using the marker peptides of the present invention, especially the peptide (1), prostate cancer patients can be detected separately from benign prostatic hyperplasia patients. By further using the peptide (4) (β2 microglobulin fragment 1) in addition thereto, accuracy of detection of prostate cancer increases. The peptide(s) to be used in prostate cancer testing may be arbitrary selected depending on the purpose of the test, and the test may be carried out using at least one peptide, for example, two or more peptides in combination, selected from the peptides described in Table 1.

The biomarker of the present invention can be used for prostate cancer testing in various situations. For example, the biomarker of the present invention can be used not only for screening for prostate cancer in medical examination and the like, but also for discrimination between prostate cancer and benign prostatic hyperplasia (detection of benign prostatic hyperplasia), monitoring of a therapeutic effect during or after treatment of prostate cancer, detection of recurrence after treatment of prostate cancer, prognostication of patients, and the like. In the present invention, the term "prostate cancer testing" includes these various tests. In the present invention, the term "prostate disease" means prostate cancer and/or benign prostatic hyperplasia. "Prostate disease testing" has the same meaning as the "prostate cancer testing" defined above, and detection of benign prostatic hyperplasia is also included within the scope of the present invention.

Subjects who are suspected of having prostate cancer based on a high PSA level, symptom of prostatic hyperplasia and/or the like in general medical examination or health screening including the conventional PSA test are supposed to be subjected to discrimination between benign prostatic hyperplasia and prostate cancer. For such patients suspected of having prostate cancer, a peptide marker that enables detection of prostate cancer patients separately from benign prostatic hyperplasia patients (for example, the peptide (1) described above) can be preferably used.

In prostate cancer testing using the biomarker of the present invention, a urine sample collected from a subject is analyzed. Although the urine sample may be a sample collected during normal urination, it is more preferred to collect the sample after prostatic massage. The prostatic massage may be carried out by a conventional method in which, for example, a finger is inserted into the rectum, and each of the left, right and center portions of the prostate is massaged about 3 times from the bottom to the apex.

The method of analyzing a urine sample is not limited, and any known method may be employed. Examples of the method for analyzing a sample for detection of the peptide marker include established techniques such as: mass spectrometry; chromatography (e.g., liquid chromatography [LC] and gas chromatography [GC]); electrophoresis (e.g., capillary electrophoresis); immunoassay using an immune antibody; detection methods using an antibody or aptamer; use of a binding carrier including a microplate, microarray, membrane strip and beads; and use of detection principles including luminescence, fluorescence and surface plasmon resonance. These methods may also be used in an arbitrary combination in the present invention. In the present invention, "detection" includes both qualitative detection (detection of the presence or absence of a peptide) and quantitative detection (measurement of the amount of a peptide), and the quantitative detection also includes semi-quantitative detection. The detected value is represented as the signal intensity of a detected ion in mass spectrometry, and can be represented as the content of the peptide in the methods such as electrophoresis, liquid chromatography and immunoassays including ELISA. In the present invention, the unit of representation of the peptide marker is not limited as long as discrimination between a cancer patient and a non-cancer patient is possible therewith.

If necessary, the urine sample may be pretreated before analysis depending on the analysis method employed. By the pretreatment, the urinary peptide marker can be more stably analyzed. The method of pretreatment per se is a conventional method, and examples of the method include removal of cell components, concentration through a molecular sieve membrane, concentration with a peptide-adsorbing carrier, and fractionation by ion-exchange treatment. One of such pretreatments may be carried out, or two or more of such pretreatments may be carried out in combination. Since the peptide marker of the present invention has a molecular weight of not more than 10,000, examples of potentially useful methods for pretreatment of a urine sample in the test method of the present invention include a pretreatment in which the region of molecular weights of not more than 10,000, especially the region of molecular weights of 1000 to 5000, is collected by fractionation through a molecular sieve membrane (e.g., flat membrane or hollow fiber membrane) to achieve concentration and separation of the peptide marker, and a pretreatment in which adsorptive separation is performed using a porous resin which covers the molecular weight region described above and has an ion-exchange base introduced thereto.

Examples of the mass spectrometry include Laser-Desorption/Ionization Time-of-Flight/Mass Spectrometry (LDI-TOF/MS) and Electro-Spray Ionization Mass Spectrometry (ESI-MS). For both methods, analysis instruments are commercially available, and the methods can be easily carried out by those skilled in the art.

In the TOF/MS method, the marker peptide of interest can be detected by pattern analysis of a spectrum obtained by a TOF/MS instrument. Qualitative detection of whether the peptide is present in a urine sample or not is possible based on whether a peak having a specific m/z value shown in Table 1 above is present or not, and quantitative detection is also possible based on the height of the m/z peak in the spectrum. Since the m/z value may have a certain error depending on the instrument used and the like, values are indicated in Table 1 considering such an error. Specific examples of LDI-TOF/MS include Matrix-Assisted Laser Desorption/Ionization Time-of-Flight/Mass spectrometry (MALDI-TOF/MS) and Surface Enhanced Laser Desorption/Ionization Time-of-Flight/Mass spectrometry (SELDI-TOF/MS).

MALDI-TOF/MS is a proteome analysis method by the combination of MALDI and TOF/MS. The Examples below describe a specific example of use of this analysis method. The method may be carried out by subjecting a urine sample to appropriate pretreatment (removal of impurities, denaturation/concentration/desalting of a protein, purification, and/or the like) to provide an assay sample, adding a solution of a matrix such as α-cyano-4-hydroxycinnamic acid (CHCA) or dihydroxybenzoic acid (DHB) to this sample, and then applying the sample to a MALDI-TOF/MS system.

SELDI-TOF/MS is a protein chip technology by the combination of SELDI and TOF/MS. The method may be carried out by subjecting a urine sample to appropriate pretreatment to provide an assay sample, applying the assay sample to a protein chip to allow adsorption of the marker peptide to the chip, and then loading the chip into a SELDI-TOF/MS instrument. A chip on which a functional group such as a hydrophobic group, ion-exchange group or metal ion-immobilized group is immobilized, or a chip on which a binding molecule specific to the marker peptide of interest (e.g., antibody, antibody fragment or aptamer) is immobilized may be prepared by a conventional method, and used.

In the case of ESI-MS, separation means such as a high-performance liquid chromatography or gas chromatography directly connected to a mass spectrometer is preferably used. Since the marker peptide of the present invention has a relatively low molecular weight, detection of the marker peptide using ESI-MS is preferably carried out using the separation means under conditions suitable for separation of low-molecular-weight peptides.

In cases where the detection of a marker peptide is carried out by an immunoassay using an immune antibody, any well-known immunoassay method may be applied. Immunoassay methods can be classified based on the reaction mode into the sandwich method, competition method, agglutination method, Western blotting method and the like, or can be classified based on the label employed into the radioimmunoassay, fluorescence immunoassay, enzyme immunoassay (EIA), biotin immunoassay and the like. All of these are included in the "immunoassay", and may be used for detection of the peptide marker of the present invention. Specific examples of the method that may be used include, but are not limited to, ELISA, immunonephelometry (TIA method), latex immunoagglutination method (LATEX method), electrochemiluminescence immunoassay (ECLIA method) and immunochromatography. Further examples of the method that may be used include the microarray method (protein chip method), in which the protein of interest is detected using an antibody immobilized on glass or polymer array, and the membrane strip method and the immunobeads method. Another example that may be used is the multiplex assay, in which a plurality of biomarkers are simultaneously measured. Examples of the multiplex assay include: a method in which a plurality of types of antibodies are spotted and immobilized in each well of a 96-well plate, and luminescences produced in the same well are separately detected, wherein the basic principle is the ELISA method but the detection is carried out using ECL; and the bead array method, in which the ELISA method and the flow cytometry technology are combined, using fluorescent dye beads on which a plurality of types of antibodies are individually bound.

Methods for preparing an antibody or its antigen-binding fragment are also well known. The antibody may be either a polyclonal antibody or monoclonal antibody, and is preferably a monoclonal antibody from the viewpoint of reproducibility and the like. The antibody can be prepared by the well-known hybridoma method. More specifically, using a peptide prepared by chemical synthesis or a genetic engineering method as an immunogen, an animal (excluding human) is immunized with the immunogen, together with an adjuvant as required, to induce antibodies in the animal body. Antibody-producing cells such as spleen cells or lymphocytes are recovered from the animal and fused with immortalized cells such as myeloma cells, and thus hybridomas can be prepared. By using the peptide to be detected as a screening antigen, a hybridoma that binds to the marker peptide of interest is selected, and the selected hybridoma is grown. From the resulting culture supernatant, an anti-marker-peptide antibody can be obtained. If necessary, the binding capacity to the original full-length protein of the marker peptide, or a fragment of the original protein longer than the marker peptide, may be confirmed to select an antibody having high specificity to the marker peptide.

The "antigen-binding fragment" means an antibody fragment maintaining the binding capacity to the corresponding antigen of the antibody (antigen-antibody reactivity), such as the Fab fragment or $F(ab')_2$ fragment of immunoglobulin. It is well known that such antigen-binding fragments can also be used in immunoassays, and the fragments are useful similarly to their original antibodies. Fab fragments and $F(ab')_2$ fragments can be obtained by, as is well known, treating monoclonal antibodies with a protease such as papain or pepsin. The antigen-binding fragment is not limited to Fab fragments and $F(ab')_2$ fragments, and may be any fragment maintaining a binding capacity to its corresponding antigen, and may be one prepared by a genetic engineering method. For example, an antibody prepared by expression of its single chain fragment of variable region (scFv) in *E. coli* by a genetic engineering method may be used. The method for preparing an scFv is also well known. An scFv can be prepared by extracting mRNA from a hybridoma prepared as described above, preparing single-stranded cDNA therefrom, performing PCR using primers specific to the H-chain and L-chain of immunoglobulin to amplify the immunoglobulin H-chain gene and L-chain gene, linking these genes via a linker, introducing the resultant to a plasmid vector after adding appropriate restriction sites thereto, transforming *E. coli* with the resulting plasmid vector, and recovering scFv from the resulting *E. coli*. Such an scFv is also included in the "antigen-binding fragment".

For detection of the peptide of the present invention, an aptamer having a binding capacity to the peptide may also be used. The aptamer is produced by synthesizing DNA or RNA or a derivative thereof capable of binding to the peptide, based on the sequence information of the peptide. Measurement of the peptide is carried out by detection of binding of the aptamer by the luminescence method, fluorescence method or surface plasmon resonance method. Further examples other than the use of an aptamer include electrophoresis, LC method and GC method. All of the methods are per se well-known, conventional methods, and may be directly applied to detection of the marker peptide of the present invention.

In cancer tests using the marker peptide of the present invention, reference values may be preliminarily determined for each marker. A healthy reference value, unhealthy reference value, cancer reference value, non-cancer reference value, hyperplasia reference value, non-hyperplasia reference value and/or the like may be set depending on properties of the marker peptide.

For example, the PSA fragment 1 with m/z 2332±4 (SEQ ID NO:1) is detected at a high level in urine of prostate cancer patients, but at a low level in non-prostate cancer patients. Thus, for this marker peptide, a "non-cancer reference value", which allows judgment that the subject is unlikely to have prostate cancer in cases where the detected value is lower than this value, and a "cancer reference value", which allows judgment that the subject is likely to have prostate cancer in cases where the detected value is higher than this value, may be set. The "cancer reference value" herein may be, for example, a value which is twice as high as the average of the urinary peptide level in a population of known non-prostate cancer patients who are certainly not suffering from prostate cancer.

The urinary peptide level may be preliminarily measured for a plurality (preferably as many as possible) of populations of healthy individuals, populations of patients definitely diagnosed with prostate cancer and populations of patients definitely diagnosed with benign prostatic hyperplasia, and the average values and standard deviations may be determined to set various reference values. Such reference values may be determined for each analysis method to be employed for detection of the peptide. It has been proposed in conventional PSA tests that the reference values should be set in consideration of the age (see, for example, JAMA (1993), 270(7), p. 860-864; J Urol (1995), 153(4), p.

1160-1163; and Urol Clin N Am 30 (2003), p. 677-686). Also in the present invention, each reference value may be set in consideration of the age. That is, different reference values may be used depending on the age of the subject. For example, a reference value for young subjects (younger than 60 years old) and a reference value for old subjects (60 years old or older) may be set, or different reference values may be set for groups of ages in steps of 5 years or 10 years such that a reference value for subjects in their 40s or younger, a reference value for subjects in their 50s, a reference value for subjects in their 60s, and a reference value for subjects in their 70s and older are provided.

EXAMPLES

The present invention is described below in more detail by way of Examples. However, the present invention is not limited to the Examples below.

Identification of Urinary Prostate Cancer Diagnostic Markers Using Ion-Exchange Resin Urine (mainly post-prostatic massage urine) was collected from males after obtaining informed consent, denatured using 9 M urea solution, and then concentrated and desalted using a weak cation-exchange resin (Carboxy methyl [CM-] Sepharose Fast Flow [GE Healthcare, Freiburg, Germany]). From the mass profiles of the eluted sample, peaks specific to prostate cancer were detected, and the detected peaks were identified.

[Methods]

Urine was collected from males after obtaining informed consent. On a 50-mL centrifuge tube, a 100-μm Nylon cell strainer (BD Falcon, REF352360) was placed, and the collected urine was made to pass through the cell strainer and recovered. The recovered urine was then centrifuged at 20° C. for 10 minutes at 2,000×g (it is desirable to complete the process from urine collection to centrifugation in 30 minutes). Thereafter, the resulting supernatant was again made to pass through a 100-μm Nylon cell strainer and collected, to provide a urine sample. The analysis sample was aliquoted in 1.0-mL volumes into 1.5-mL microtubes, and stored at −80° C. until analysis.

The collection of a urine sample was mainly carried out after prostatic massage. The method of collecting a urine sample by prostatic massage was as follows. A finger was inserted into the rectum, and each of the left, right and center portions of the prostate was massaged about 3 times from the bottom to the apex, followed by collecting urine.

The urine sample to be used in the analysis was dissolved at 20° C. while performing centrifugation at 1,000×g. To 1.0 mL of the dissolved urine sample, 400 μL of a denaturing buffer (9 M urea, 2% CHAPS, 50 mM Tris, pH 9.0) was added, and the resulting mixture was stirred well, followed by allowing denaturation of peptides and proteins at 4° C. using a rotary mixer (NRC-20D, Nisshin Rika) for 30 minutes.

To 3.6 mL of a binding and washing buffer (100 mM ammonium acetate buffer, pH 4.0, 0.05% Triton-X100), 1.4 mL of the denatured solution was added, and the resulting mixture was stirred, followed by adding thereto 60 μL of 33% slurry of activated CM-Sepharose. The resulting mixed solution was stirred using a rotary mixer at room temperature for 30 minutes.

Centrifugation of 5 mL of the mixed solution was performed at 20° C. for 10 minutes at 1,000×g, and the resulting supernatant was discarded. The precipitate of CM-Sepharose was transferred to a 1.5-mL microtube, and washed 3 times with the above-described binding and washing buffer and then 3 times with ultrapure water. In the washing, centrifugation was carried out at 20° C. for 3 minutes at 2,000×g, and only the supernatant was discarded using a pipetter so that the resin would not be suspended. Finally, a trifluoroacetic acid solution (TFA, Wako Pure Chemical Industries, Ltd., Osaka, Japan) was used to elute peptides and proteins. The eluted supernatant was centrifuged at 20° C. for 5 minutes at 15,000×g, to provide the clean supernatant as a sample for mass spectrometry.

MALDI-TOF/MS$^n$ analysis was carried out using as matrices α-cyano-4-hydroxycinnamic acid (CHCA: 5 mg/tube, LaserBio Labs, Sophia Antipolis, France) and dihydroxybenzoic acid (DHB, 5 mg/tube, LaserBio Labs, Sophia Antipolis, France). Each matrix was dissolved in 500 μL of 50% acetonitrile (ACN, Wako Pure Chemical Industries, Ltd., Osaka, Japan) solution in water/0.1% TFA, and premixed with an equal amount of the sample for mass spectrometry, followed by applying 0.5 μL of the resulting mixture to an SUS sample plate for MALDI-TOF/MS. After air-drying the plate, 0.5 μL of the mixture was applied again to the plate, to provide a sample for analysis.

[Results]

Figure 1:
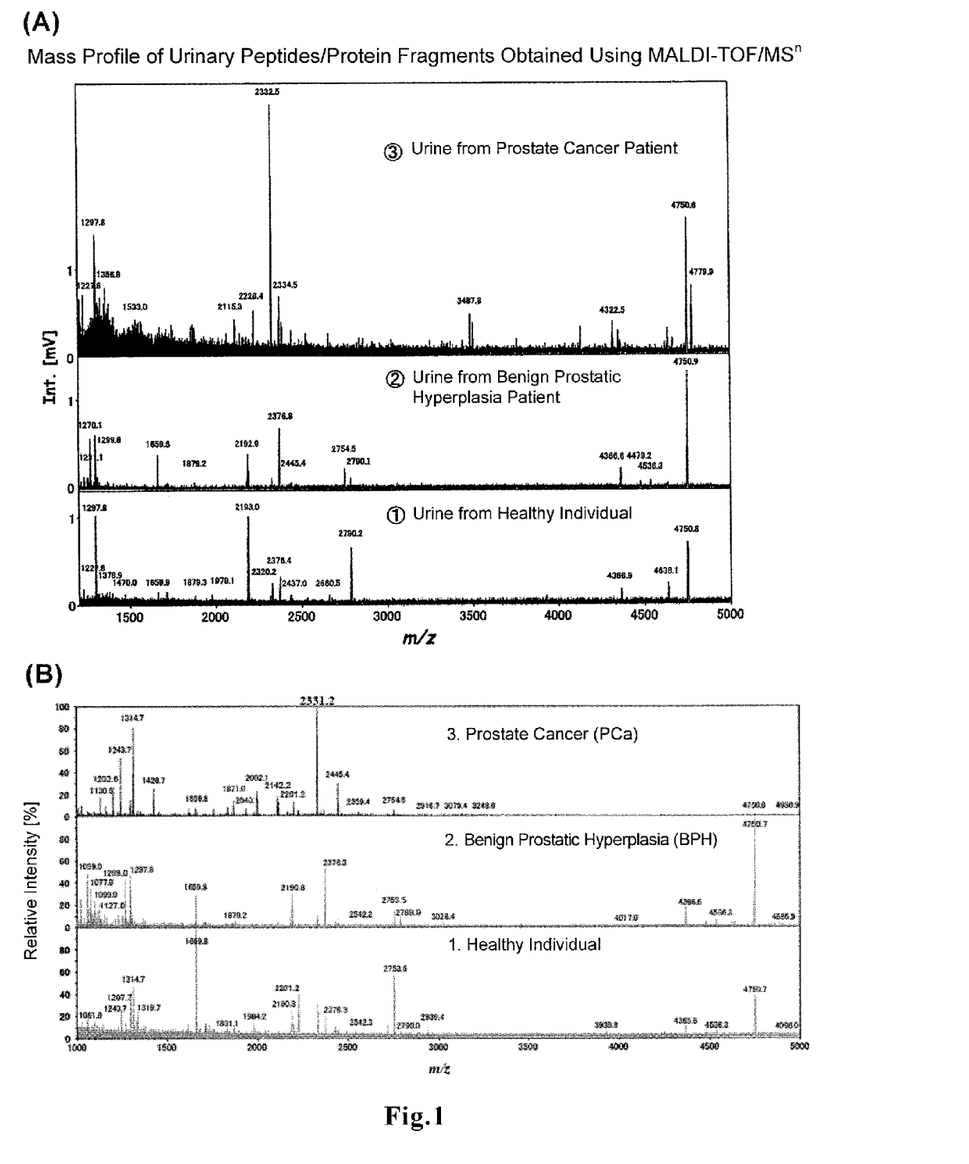
FIG. 1 shows two representative data of mass spectrometry of urine samples (post-prostatic massage urine) from healthy individuals, patients with benign prostatic hyperplasia and patients with prostate cancer.

1. Mass Profile of Urinary Peptides/Protein Fragments Obtained Using MALDI-TOF/MS$^n$ FIG. 1 shows representative examples of mass spectrometry data obtained for urine samples (post-prostatic massage urine) from healthy individuals, benign prostatic hyperplasia patients and prostate cancer patients. Data were shown such that the abscissa represents the mass (m/z value) and that the ordinate represents the peak which reflects the amount of each analyte that reached the detector at the corresponding mass. As is evident from FIG. 1, comparison of the urine samples from prostate cancer patients and benign prostatic hyperplasia patients revealed a significant increase in m/z 2332 in the prostate cancer patients. In the healthy individuals, the m/z 2332 peak, which was remarkably found in prostate cancer patients, could be hardly detected.

2. Identification of Peak for Each Urinary Peptide/Protein Fragment Using MALDI-TOF/MS$^n$ Urinary peptides/protein fragments were identified using MALDI-TOF/MS$^n$ manufactured by Shimadzu Corporation. In the analysis, a precursor ion was selected in MS$^1$, and MS$^2$ ion data obtained by MS$^2$ analysis were subjected to Mascot (trademark) MS$^2$ Ion Search (Matrix Science, Inc., Boston, Mass., USA) to carry out identification.

(1) Identification of m/z 2332

Figure 2:
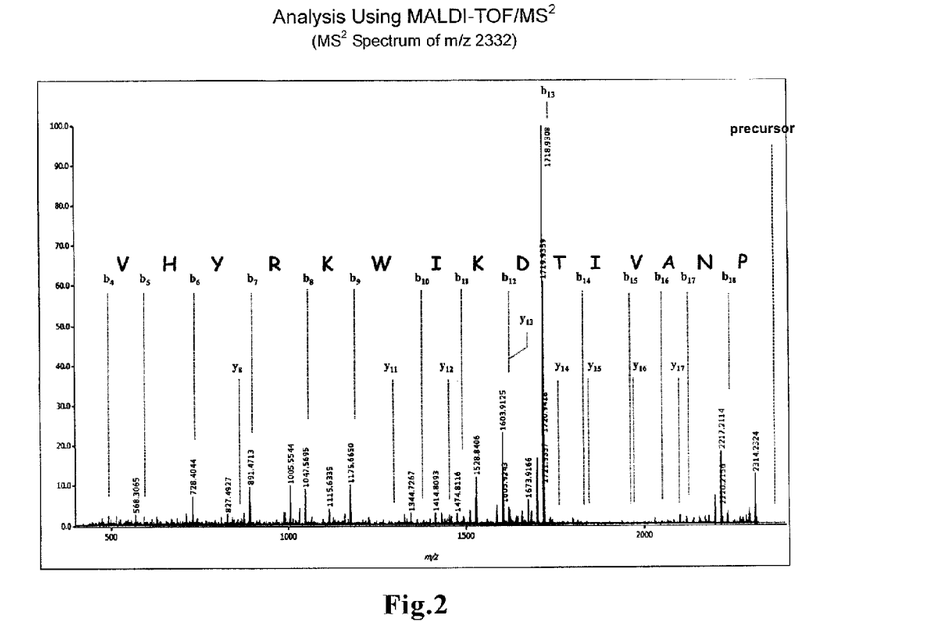
FIG. 2 is a diagram illustrating the results of identification of an amino acid sequence using m/z 2332 as a precursor ion.

FIG. 2 shows the result of identification of the amino acid sequence using m/z 2332 as a precursor ion. As a result of Mascot (trademark) MS$^2$ Ion Search, m/z 2332 was found to be a C-terminal fragment of PSA, which has a molecular weight of 2331 Da. The amino acid sequence at the C-terminus of PSA assumed by Mascot (trademark) MS$^2$ Ion Search (YTKVVHYRKWIKDTIVANP, SEQ ID NO:1) was synthesized (Medical & Biological Laboratories Co., Ltd. [MBL], Nagoya, Japan), and subjected to a validation test. The MS$^2$ mass profile of the synthetic peptide having the assumed amino acid sequence was identical to the MS² mass profile of m/z 2332 detected in urine of the prostate cancer patients. As a result of this analysis, m/z 2332 in urine of the prostate cancer patients was demonstrated to be identical to the amino acid structure at the C-terminus of PSA. In order to clarify the origin of the C-terminal fragment of PSA having a molecular weight of 2331 Da, a comparison was made between post-prostatic massage urine and spot urine from the prostate cancer patient. As a result, a remarkable m/z 2332 peak was detected in the post-prostatic massage urine. Although this peak can also be detected in post-prostatic massage urine obtained from a benign prostatic hyperplasia patient, the peak shows a significantly low value. From the above results, the m/z 2332 peak was identified to be a C-terminal fragment of PSA whose secretion from the prostate was remarkably promoted by prostatic massage in a prostate cancer patient.

(2) Identification of m/z 1243

Figure 3:
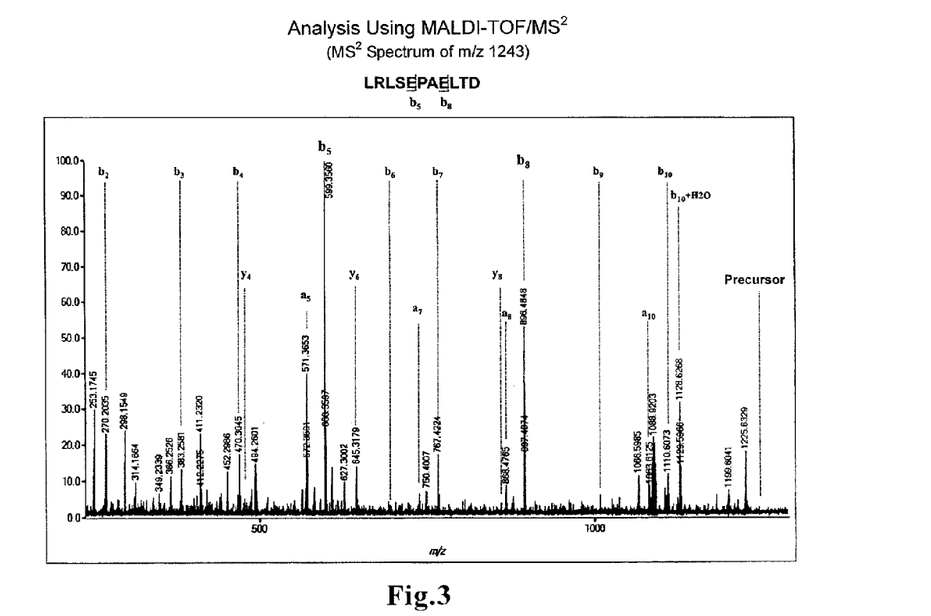
FIG. 3 is a diagram illustrating the results of identification of an amino acid sequence using m/z 1243 as a precursor ion.

FIG. 3 shows the result of identification using m/z 1243 as a precursor ion. As a result of Mascot (trademark) MS² Ion Search, m/z 1243 was identified to be a PSA fragment having a molecular weight of 1242 Da (LRLSEPAELTD, SEQ ID NO:2).

(3) Identification of m/z 1314

Figure 4:
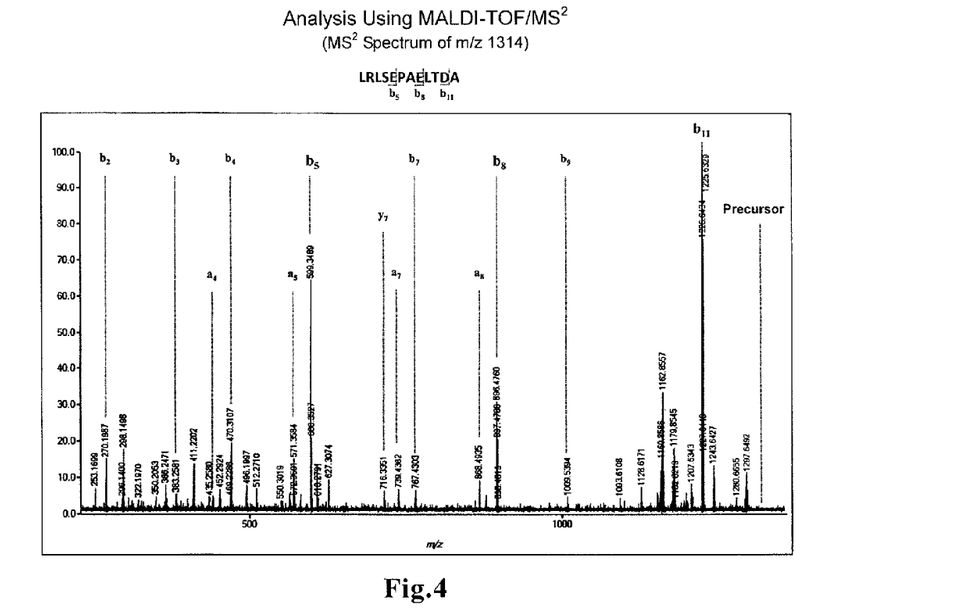
FIG. 4 is a diagram illustrating the results of identification of an amino acid sequence using m/z 1314 as a precursor ion.

FIG. 4 shows the result of identification using m/z 1314 as a precursor ion. As a result of Mascot (trademark) MS² Ion Search, m/z 1314 was identified to be a PSA fragment having a molecular weight of 1313 Da (LRLSEPAELTDA, SEQ ID NO:3).

(4) Identification of m/z 2444

Figure 5:
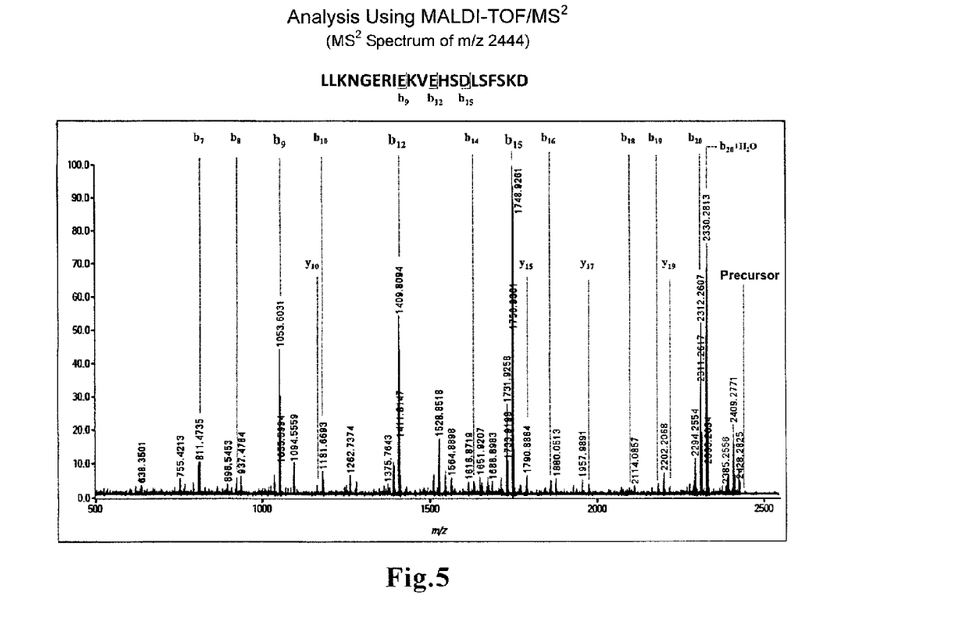
FIG. 5 is a diagram illustrating the results of identification of an amino acid sequence using m/z 2444 as a precursor ion.

FIG. 5 shows the result of identification using m/z 2444 as a precursor ion. As a result of Mascot (trademark) MS² Ion Search, m/z 2444 was identified to be a β2 microglobulin (β2M) fragment having a molecular weight of 2443 Da (LLKNGERIEKVEHSDLSFSKD, SEQ ID NO:4).

3. Relative Quantification of Each Peak Calculated from Mass Profile of Urinary Peptides/Protein Fragments Obtained by MALDI-TOF/MS"

The relative quantitative value of each peak in the mass profile of urinary peptides/protein fragments obtained by MALDI-TOF/MS" was calculated for 1 case of urine from a healthy individual, 4 cases of urine from benign prostatic hyperplasia patients, and 10 cases of urine from prostate cancer patients. That is, the total ion current (TIC) within the range of m/z 1200 to 5000 was used for normalization, and the relative quantitative value was expressed as the ratio (%) of the current occupied by each peak. The results are shown in Table 2. "Cancer" represents the group of prostate cancer patients, and "Non-cancer" represents the group of healthy individuals and benign prostatic hyperplasia patients.

4. Detection of Prostate Cancer Patients Using PSA C-terminal Peptide (m/z 2332)

The PSA fragment 1 with m/z 2332, which was composed of the C-terminal region of PSA, was statistically analyzed in more detail with an increased number of cases. In the same manner as described above, post-prostatic massage urine was collected from each case shown in Table 3, and subjected to MALDI-TOF/MS", followed by calculating the relative quantitative value of each peak in the mass profile of the PSA fragment 1. Comparison among the groups was carried out by the Mann-Whitney U test. As a Comparative Example, a conventional PSA test was also carried out by measuring the serum PSA level in each case.

TABLE 3

| Subject group | | Years Old |
|---|---|---|
| Non-prostate cancer | (n = 17) | 65.0 ± 7.9 |
| Healthy | (n = 9) | 70.0 ± 10.4 |
| Benign prostatic hyperplasia | (n = 8) | 65.0 ± 4.3 |
| Prostate cancer | (n = 14) | 68.0 ± 6.8 |
| | | (Median ± SD) |

Figure 6:
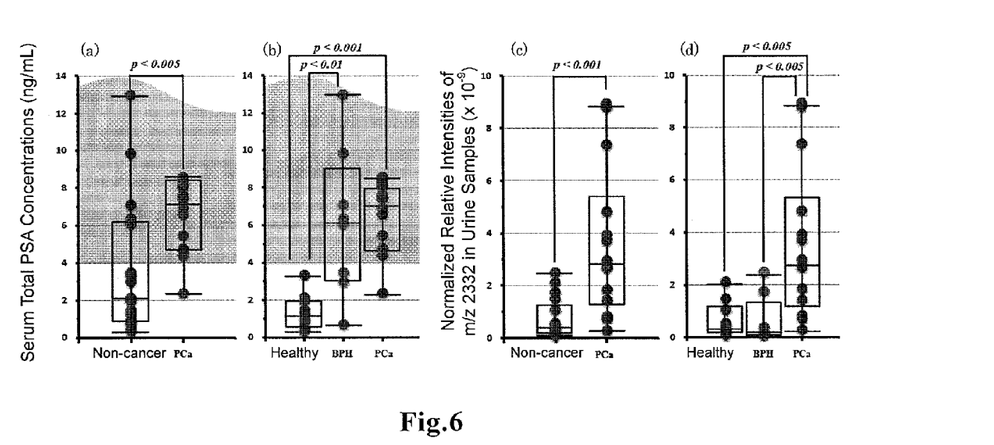
FIG. 6 is a diagram illustrating the results of comparison of the urinary m/z 2332 peptide level and the serum PSA level between 17 cases of non-cancer patients (9 cases of healthy individuals and 8 cases of benign prostatic hyperplasia patients) and 14 cases of prostate cancer patients. (a) shows the results of comparison of the serum PSA level between the non-cancer patient group and the prostate cancer patient group; (b) shows the results of comparison of the serum PSA level among the healthy group, the benign prostatic hyperplasia patient group and the prostate cancer patient group; (c) shows the results of comparison of the urinary m/z 2332 peptide level (relative level) between the non-cancer patient group and the prostate cancer patient group; and (d) shows the results of comparison of the urinary m/z 2332 peptide level (relative level) among the healthy group, benign prostatic hyperplasia patient group and prostate cancer patient group. The gray areas in (a) and (b) (not less than 4.0 ng/mL) are areas where the level is judged to be abnormal in cancer tests based on the serum PSA level.

The results are shown in FIG. 6. In the conventional PSA test, a significant difference was found between the non-prostate cancer group and the prostate cancer group (p<0.005, FIG. 6a). However, analysis of the 3 groups, that is, the healthy group, the benign prostatic hyperplasia group and the prostate cancer group, showed no significant difference between the benign prostatic hyperplasia group and the prostate cancer group, and hence benign prostatic hyperplasia and prostate cancer could not be discriminated from each other (FIG. 6b). On the other hand, the urinary level of the PSA fragment 1 with m/z 2332 (SEQ ID NO:1) made it possible to discriminate not only between the non-prostate cancer group and the prostate cancer group (p<0.001, FIG. 6c) but also between the benign prostatic hyperplasia group and the prostate cancer group (p<0.005, FIG. 6d).

Figure 7:
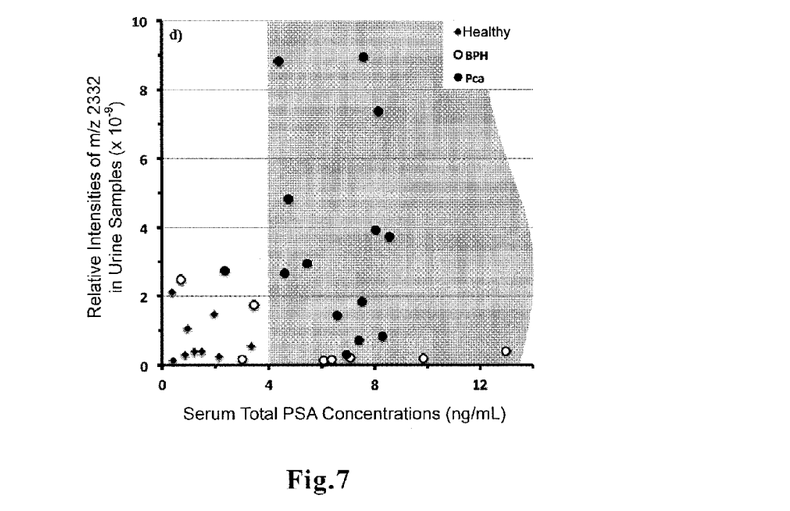
FIG. 7 is a graph illustrating comparison of the results of a conventional PSA test (abscissa) and the results of a test method using the PSA fragment 1 with m/z 2332 (ordinate). The gray area in the figure (not less than 4.0 ng/mL) represents the area where the level is judged to be abnormal in cancer tests based on the serum PSA level.

FIG. 7 is a graph illustrating comparison of the results of the conventional PSA test (abscissa) and the results of the test method using the PSA fragment 1 with m/z 2332 (ordinate). In the conventional PSA test, serum PSA levels ranging from 4 to 10 ng/mL were in the gray zone, and more than half of the cases of benign prostatic hyperplasia (BPH) also fell within the gray zone. In contrast, the test method based on the urinary level of the PSA fragment 1 was excellent in detection sensitivity for prostate cancer, and confirmed to have high detection sensitivity especially in the gray zone of the serum PSA level.

TABLE 2

| | Biomarker peptide | | | |
|---|---|---|---|---|
| Sample | m/z 1243 PSA fragment 2 | m/z 1314 PSA fragment 3 | m/z 2332 PSA fragment 1 | m/z 2444 β2M fragment 1 |
| Prostate cancer patient (N = 10) | 0.600 ± 0.519 | 0.744 ± 0.804 | 2.96 ± 2.46 | 0.456 ± 0.332 |
| Non-prostate cancer patient (N = 5) | 0.177 ± 0.055 | 0.197 ± 0.059 | 0.507 ± 0.175 | 0.181 ± 0.047 |
| p value* | 0.014 | 0.045 | 0.006 | 0.021 |
| Cancer/non-cancer (ratio of average) | 3.40 | 3.78 | 5.83 | 2.52 |

The invention claimed is:

1. A method comprising:
   treating a subject suspected of having or diagnosed with prostate disease; analyzing a urine sample collected from the subject, wherein the urine sample is subjected to centrifugation, denaturation, weak cation-exchange resin treatment, and then analyzed by mass spectrometry; and
   examining the urine sample for the presence or absence or the amount of at least one urinary peptide selected from the peptides (a) to (d) below:
   (a) peptide consisting of the amino acid sequence of SEQ ID NO:1;
   (b) peptide consisting of the amino acid sequence of SEQ ID NO:2;
   (c) peptide consisting of the amino acid sequence of SEQ ID NO:3;
   (d) peptide consisting of the amino acid sequence of SEQ ID NO:4.

2. A method comprising:
   treating a subject suspected of having or diagnosed with prostate cancer; analyzing a urine sample collected from the subject, wherein the urine sample is subjected to centrifugation, denaturation, weak cation-exchange resin treatment, and then analyzed by mass spectrometry; and examining the urine sample for the presence or absence or the amount of
at least one urinary peptide selected from the peptides (a) to (d) below:
(a) peptide consisting of the amino acid sequence of SEQ ID NO:1;
(b) peptide consisting of the amino acid sequence of SEQ ID NO:2;
(c) peptide consisting of the amino acid sequence of SEQ ID NO:3;
(d) peptide consisting of the amino acid sequence of SEQ ID NO:4.

3. The method according to claim 1, wherein said urine sample is a urine sample collected from the subject after prostatic massage.

4. The method according to claim 1, wherein the presence or absence or the amount of urinary peptide (a) is examined by detecting a peptide whose m/z is 2332±4 by mass spectrometry.

5. A method comprising:
analyzing a urine sample collected from a subject, wherein the urine sample is subjected to centrifugation, denaturation, weak cation-exchange resin treatment, and then analyzed by mass spectrometry;
detecting whether or how much at least one urinary peptide is present in the urine sample, wherein said at least one urinary peptide is selected from the peptides (a) to (d) below:
(a) peptide consisting of the amino acid sequence of SEQ ID NO:1;
(b) peptide consisting of the amino acid sequence of SEQ ID NO:2;
(c) peptide consisting of the amino acid sequence of SEQ ID NO:3;
(d) peptide consisting of the amino acid sequence of SEQ ID NO:4.

6. The method according to claim 5, wherein a urine sample collected from a subject suspected of having prostate cancer is analyzed.

7. A method comprising:
analyzing a urine sample collected from a human subject; and
examining the urine sample for the presence or absence or the amount of at least one urinary peptide by an immunoassay using a non-human animal antibody that binds to at least one urinary peptide,
wherein said at least one urinary peptide is selected from the peptides (a) to (d) below:
(a) peptide consisting of the amino acid sequence of SEQ ID NO:1;
(b) peptide consisting of the amino acid sequence of SEQ ID NO:2;
(c) peptide consisting of the amino acid sequence of SEQ ID NO:3;
(d) peptide consisting of the amino acid sequence of SEQ ID NO:4.

8. The method according to claim 1, wherein the urine sample is subjected to removal of cell components and then analyzed.

9. The method according to claim 1, wherein the urine sample is subjected to centrifugation within 30 minutes from collection of the urine sample.

* * * * *